United States Patent [19]

Neunhoeffer et al.

[11] Patent Number: 5,534,267
[45] Date of Patent: Jul. 9, 1996

[54] COMPOSITION FOR THE OXIDATIVE DYEING OF HAIR CONTAINING 4,5-DIAMINOPYRAZOLE DERIVATIVES AS WELL AS NEW 4,5-DIAMINOPYRAZOLE DERIVATIVES AND PROCESS FOR THEIR SYNTHESIS

[75] Inventors: Hans Neunhoeffer, Mühltal; Stefan Gerstung, Reinheim; Thomas Clausen; Wolfgang R. Balzer, both of Alsbach, all of Germany

[73] Assignee: Wella Aktiengesellschaft, Darmstadt, Germany

[21] Appl. No.: 244,729

[22] PCT Filed: Sep. 29, 1993

[86] PCT No.: PCT/EP93/02641

§ 371 Date: Jun. 7, 1994

§ 102(e) Date: Jun. 7, 1994

[87] PCT Pub. No.: WO94/08970

PCT Pub. Date: Apr. 28, 1994

[30] Foreign Application Priority Data

Oct. 16, 1992 [DE] Germany ............... 42 34 887.0

[51] Int. Cl.$^6$ .................. A61K 7/13; C07D 231/38
[52] U.S. Cl. ................ 424/701; 548/371.4; 8/409
[58] Field of Search ............. 8/405–409, 414–416, 8/421–425, 428–429, 442; 548/371.4; 424/70.1

[56] References Cited

U.S. PATENT DOCUMENTS 5,061,289  10/1991  Clausen et al. ............... 8/405

FOREIGN PATENT DOCUMENTS 2160317  4/1980  Germany.

OTHER PUBLICATIONS

M. A. Khan, et al, Canadian Journal of Chemistry, vol. 49, 1971, p. 3566.
K. J. Klebe, et al, Synthesis, 1973, p. 294.
J. P. H. Juffermanns, et al, Journal of Organic Chemistry 51, 1986, p. 4656.

Primary Examiner—Jyothsna Venkat
Attorney, Agent, or Firm—Michael J. Striker

[57] ABSTRACT

The composition for oxidative dyeing of hair based on a combination of developer substances and coupler substances, contains as a developer substance 4,5-diamino-1-(4'-methoxybenzyl)pyrazole, 4,5-diamino-1-(4'-methylbenzyl)pyrazole, 4,5-diamino-1-(4'-chlorobenzyl)pyrazole, 4,5-diamino-1-(3'-methoxybenzyl)pyrazole, 4-amino-1-(4'-methoxy-benzyl)-5-methylaminopyrazole or 4-amino-5-(2'-hydroxyethyl)amino-1-(4'-methoxybenzyl)pyrazole.

11 Claims, No Drawings

COMPOSITION FOR THE OXIDATIVE DYEING OF HAIR CONTAINING 4,5-DIAMINOPYRAZOLE DERIVATIVES AS WELL AS NEW 4,5-DIAMINOPYRAZOLE DERIVATIVES AND PROCESS FOR THEIR SYNTHESIS

This application is a 371 of PCT/EP93/02641 filed Sep. 29, 1993.

BACKGROUND OF THE INVENTION

The subject matter of the invention concerns compositions for the oxidative dyeing of hair based on 4,5-diaminopyrazole derivatives as developers and new 4,5-diaminopyrazole derivatives.

In the area of hair coloring, oxidative dyes have achieved considerable importance. The dyeing is effected by the reaction of certain developers with certain couplers in the presence of a suitable oxidizing agent.

Such developers are, in particular, 2,5-diaminotoluene, 2,5-diaminophenylethyl alcohol, p-aminophenol and 1,4-diaminobenzene. Resorcinol, 4-chlororesorcinol, 1-naphthol, 3-aminophenol, 5-amino-2-methylphenol and derivatives of m-phenylenediamine are preferably used as couplers.

Oxidative dye compositions for dyeing human hair have numerous special requirements. For example, they must be unobjectionable in toxicological and dermatological respects and must enable the desired intensity of coloring. In addition, a favorable fastness to light, permanent waving, acids and rubbing is required of the achieved hair dyes. But, in every instance, such hair dyes must remain stable over a period of at least 4 to 6 weeks without being affected by light, rubbing or chemical agents. Moreover, it is necessary that a wide assortment of various color shades can be produced by means of combining suitable developers and couplers. 4-Aminophenol above all is used to achieve natural shades and especially fashionable shades in the red range either by itself or in a mixture with other developers in combination with suitable couplers.

The developer 4-aminophenol, whose chief use was formerly for the red range of the color scale, has been criticized in the past with respect to its physiological compatibility, while developers such as pyrimidine derivatives which have been recommended more recently are not completely satisfactory with respect to coloring. The pyrazole derivatives described in DE-OS21 60 317 such as 3-amino-1-phenyl-2-pyrazolone-5 have insufficient depth of color when used to dye hair and are not usable in hair dyeing practice.

Pyrazole derivatives which achieve intense coloring with various couplers are described in DE-OS 38 43 892. The compounds described therein can only be obtained by very expensive synthesizing processes and have low yields.

Various methods have been described in technical literature for producing 1-methyl-4,5-diaminopyrazole. According to H. Dorn, et al., *Chem. Ber.* 98, p. 3368 (1965), 5-amino-1-methylpyrazole-4-carboxylic acid is obtained in a yield of 53 percent from ethoxymethylene cyanoacetic acid ethyl ester and methylhydrazine and is decarboxylated to obtain 5-amino-1-methylpyrazole with a yield of 75 percent (total yield : 40 percent). DE-OS 2 141 700 describes a single-step process for obtaining 5-amino-1-methylpyrazole from N,N-dimethylaminoacrylonitrile and methylhydrazine in a yield of 71 percent. For further conversion, this compound can be convened to 5-amino-1-methyl-4-nitropyrazole with a yield of 23 percent according to M. A. Khan, et al., *Can. J. Chem.* 49, p. 3566 (1971).

According to V. P. Perevalov, et al., *Khim. Geterotsicl. Soedin.* 8, p. 1090 (1985), catalytic reduction of this product produces 1-methyl-4,5-diaminopyrazole dihydrochloride with a yield of approximately 79 percent. According to this reaction sequence, the total yield of 1-methyl-4,5-diaminopyrazole amounts to 13 percent throughout all steps.

Better yields are obtained when 5-amino-1-methylpyrazole is converted with isoamyl nitrite, according to H. Dorn, et al., *Liebigs Ann. Chem.* 717, p. 118 (1968), to produce 5-amino-1-methyl-4-nitrosopyrazole (gross yield approximately 97 percent) and then reduced with tin(II)chloride to give the end product (yield: 67 percent) so that the total yield according to this process is 46 percent throughout all steps.

A corresponding synthesis for 1-benzyl-4,5-diaminopyrazole is described in DE-OS 34 32 983. 5-Amino-1-benzylpyrazole-4-carboxylic acid ethyl ester is obtained from ethoxymethylene cyanoacetic acid ethyl ester and benzylhydrazine. After cleavage of the ester, decarboxylation, nitrozation and reduction, 1-benzyl-4,5-diaminopyrazole is obtained in a total yield of 30 percent.

Aside from low yields in some cases, the described processes exhibit other disadvantages. For example, it has not been taken into account that starting compounds such as ethoxymethyl cyanoacetic acid ethyl ester and N,N-dimethylaminoacrylonitrile as well as certain hydrazine derivatives are not available commercially and in some cases must be produced by costly syntheses. Moreover, commercially available hydrazine derivatives are classified as poisonous and in some cases as suspected carcinogens. Further, the production of compounds substituted in the 5-position amino group (e.g., alkyl, hydroxyalkyl, benzyl) is not described in this process or by subsequent steps. A further disadvantage of this synthesis consists in that the ring alkylation is already introduced in the first reaction step, that is, special starting compounds are already required at the start of the synthesis.

Under these conditions, alkylation on the ring nitrogen of a pyrazole derivative substituted in the 4-position or 5-position would be more advisable so that different derivatives are achieved only at the end of the synthesis through the selection of different alkylating agents. A process for the production of 1-methyl-4,5-diaminopyrazole is described in DE-OS 38 43 892. According to this process, 3(5)-amino-4-nitropyrazole—which is formed in a total yield of approximately 41 percent by cyclization of 2-chloroacrylonitrile with hydrazine (G. Ege, *Angew. Chem.*, 86, p. 237 (1974)) and subsequent acetylation of the amino group, nitration and separation of the protective group—is alkylated with dimethyl sulfate to give an isomeric mixture in a yield of 70 percent which can be separated by chromatography to give the desired 5-amino-1-methyl-4-nitropyrazole in a yield of 25 percent and the isomeric 3-amino-1-methyl-4-nitropyrazole in a yield of 45 percent. The corresponding diamino compounds were isolated after reduction of the nitro compounds.

DE-OS 38 43 892 describes conversion of 3(5)-amino-4-nitropyrazole with benzyl bromide. The desired 5-amino-1-benzyl-4-nitropyrazole is not formed. Rather, a mixture is obtained from which approximately 18 percent 1-benzyl-3-benzylamino-4-nitropyrazole and 78 percent 3-amino-1-benzyl-4-nitropyrazole are obtained after chromatographic separation.

This process also provides very poor yield, if any, of substituted pyrazole derivatives such as 5-amino-1-alkyl-4- nitropyrazole or 5-amino-1-benzyl-4-nitropyrazole and compounds substituted in the 5-amino group which can be converted to the corresponding diamino compounds by reduction. Further, this process also requires the use of hydrazine which has been criticized.

SUMMARY OF THE INVENTION

Accordingly, it is an object of the present invention to provide an oxidative hair dye composition based on a combination of developers and couplers in which a developer is obtained for the red range which is very well tolerated physiologically, dyes the hair in brilliant red shades with a good depth of color when combined with conventional couplers, and can be produced in good yields.

It has now been found that this object is met in an outstanding manner by a composition for the oxidative dyeing of hair based on a combination of developers and couplers which contains, as developer, a 4,5-diaminopyrazole of the general formula (I),

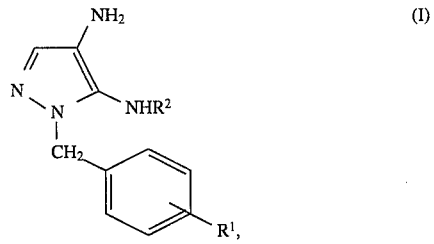

where $R^1$ represents halogen, alkyl with 1 to 4 carbon atoms or alkoxy with 1 to 4 carbon atoms and R2 represents hydrogen, alkyl with 1 to 4 carbon atoms or hydroxyalkyl with 2 to 4 carbon atoms or its physiologically tolerated, water-soluble salts.

The hair dye composition contains 0.01 to 3.0 percent by weight, preferably 0.1 to 2.5 percent by weight, of the developers of formula (I), preferably 4,5-diamino-1-(4'-methoxybenzyl)pyrazole, 4,5-diamino-1-(4'-methylbenzyl)pyrazole, 4,5-diamino-1-(3'-methoxybenzyl)pyrazole and 4,5-diamino-1-(4'-chlorobenzyl)pyrazole.

Although it would be obvious, owing to the advantageous properties of the new developers described herein, to use these developers by themselves, it is, of course, also possible to use the developers of formula (I) together with known developers such as 1,4-diaminobenzene, 2,5-diaminotoluene or 2,5-diaminophenylethyl alcohol.

Preferred couplers include α-naphthol, resorcinol, 4-chlororesorcinol, 4,6-dichlororesorcinol, 2-methylresorcinol, 2-amino-4-(2'-hydroxyethyl)aminoanisole, 2,4-diaminophenyl alcohol, m-phenylenediamine, 5-amino-2-methylphenol, 2,4-diaminophenoxyethanol, 4-amino-2-hydroxyphenoxyethanol, 3-aminophenol, 3-amino-2-methylphenol, 4-hydroxy- 1,2-methylenedioxybenzene, 4-amino- 1,2-methylenedioxybenzene, 4-(2'-hydroxyethyl)amino-1,2-methylenedioxybenzene, 2,4-diaminobenzyl alcohol, 2,4-diaminophenetole, 2,4-diamino-5-methylphenetole, 4-hydroxyindole, 3-amino-5-hydroxy-2,6-dimethoxypyridine and 3,5-diamino-2,6-dimethoxypyridine.

The couplers and developers can be contained in the hair dye composition individually or in combination.

The total quantity of combined developers and couplers contained in the hair dye composition herein described is 0.1 to 5.0 percent by weight, particularly 0.5 to 4.0 percent by weight. The developers are generally used in approximately equimolar amounts with respect to the couplers. However, it is not disadvantageous in this respect if the quantity of developers is somewhat greater or less than that of the couplers.

Further, the hair dye composition according to the invention can also contain other dyeing components, e.g. 6-amino-2-methylphenol and 2-amino-5-methylphenol, as well as conventional direct dyes, e.g. triphenylmethane dyes such as Diamond Fuchsine (C.I. 42,510), (4-[(4'-aminophenyl)-(4"-imino-2",5"-cyclohexadiene-1-ylidene)methyl]-2-methylaminobenzene monohydrochloride) and Leather Ruby HF (C.I. 42,520), (4-[(4'-amino-3'-methylphenyl) -(4"-imino-3"-methyl-2",5"-cyclohexadiene-1"-ylidene) -methyl]-2-methylaminobenzene monohydrochloride), aromatic nitro dyes such as 2-nitro-1,4-diaminobenzene, 2-amino-4-nitrophenol, 2-amino-5-nitrophenol, 2-amino-4, 6-dinitrophenol, 2-amino-5-(2'-hydroxethyl)aminonitrobenzene and 2-methylamino-5-bis-(2'-hydroxyethyl)aminonitrobenzene, azo dyes such as Acid Brown 4 (C.I. 14,805) (6-[(4'-aminophenyl)azo]-5-hydroxynaphthalene-1-sulfonic acid sodium salt) and dispersed dyes such as 1,4 -diaminoanthraquinone and 1,4,5,8-tetraaminoanthraquinone. The hair dye compositions can contain these dye components in quantities of approximately 0.1 to 4.0 percent by weight.

Of course, the couplers and developers as well as the other dye components, insofar as they are bases, can also be used in the form of physiologically tolerated salts with organic or inorganic acids such as hydrochloric acid or sulfuric acid or —insofar as they have aromatic OH groups —in the form of salts with bases, e.g. as alkali phenolates.

Further, the hair dye composition can contain additional common cosmetic ingredients, e.g. antioxidants such as ascorbic acid, thiogylcolic acid or sodium sulfite, as well as perfume oils, complexing agents, wetting agents, emulsifiers, thickeners and hair conditioning substances.

The new hair dye composition may be in the form of a solution for example, particularly an aqueous or aqueous-alcoholic solution. But particularly preferred preparation forms are creams, gels or emulsions. The composition contains a mixture of dye components and the usual ingredients for such preparations.

For example, common ingredients in solutions, creams, emulsions or gels are solvents such as water, lower aliphatic alcohols, e.g. ethanol, propanol and isopropanol, glycerol or glycols such as 1,2-propylene glycol, wetting agents or emulsifiers from the classes of anionic, cationic, amphoteric or nonionic surface-active substances such as fatty alcohol sulfates, ethoxylated fatty alcohol sulfates, alkyl sulfonates, alkyl benzene sulfonates, alkyl trimethylammonium salts, alkyl betaines, ethoxylated fatty alcohols, ethoxylated nonylphenols, fatty acid alkanol amides, ethoxylated fatty acid esters, and thickeners such as higher fatty alcohols, starch, cellulose derivatives, petrolatum, paraffin oil and fatty acids, as well as hair conditioning substances such as cationic resins, lanolin derivatives, cholesterol, pantothenic acid and betaine. These components are used in conventional quantities for such purposes. For example, the wetting agents and emulsifiers are used in concentrations of approximately 0.5 to 30 percent by weight, the thickeners are used in quantities of approximately 0.1 to 25 percent by weight and the hair grooming agents are used in concentrations of approximately 0.1 to 5.0 percent by weight.

Depending on the composition, the hair dye composition according to the invention can have a weak acidic, neutral or alkaline reaction. In particular, it has a pH of 6.0 to 11.5 which is adjusted in the alkaline range with ammonia. However, organic amines such as monoethanolamine and triethanolamine or inorganic bases such as sodium hydroxide and potassium hydroxide can also be used. To adjust the pH in the acidic range, phosphoric acid and acetic acid or other organic acids such as citric acid or tartaric acid can be used.

When used for oxidative dyeing of hair, the aforementioned hair dye composition is mixed immediately prior to use with an oxidizing agent and a quantity of this mixture sufficient for the hair dyeing treatment, generally approximately 60 to 200 g depending on the fullness of the hair, is applied to the hair.

Hydrogen peroxide or its addition compounds in urea, melamine or sodium borate in the form of a 3- to 12-percent aqueous solution, preferably a 6-percent aqueous solution, are the principle oxidizing agents selected for the development of the hair coloring, although atmospheric oxygen can also be used. If a 6-percent hydrogen peroxide solution is used as oxidizing agent, the weight ratio of hair dye composition to oxidizing agent is 5:1 to 1:2, but preferably 1:1. Larger quantities of oxidizing agent are used chiefly when there are higher concentrations of dyestuff in the hair dye composition or when a more intensive bleaching of the hair is intended simultaneously. The mixture is allowed to act on the hair at 15° to 50° C. for approximately 10 to 45 minutes, preferably 30 minutes. The hair is then rinsed with water and dried. The hair is washed with a shampoo after this rinse, if necessary, and possibly rinsed again with a weak organic acid such as citric acid or tartaric acid. The hair is then dried.

The 4,5-diaminopyrazole derivatives of the general formula (I) used in the oxidative hair dye compositions according to the invention can be produced in an advantageous manner by initiating a reaction of a 3,5-dibromo-4-nitropyrazole of the general formula (II) with a suitable benzyl halide in the presence of sodium hydride. The obtained 1-benzyl-3,5-dibromo-4-nitropyrazole derivative of the general formula (III) is then converted with an amine and the 5-alkylamino-1-benzyl-3-bromo-4-nitropyrazole derivative of general formula (IV) which is obtained in this way is catalytically reduced.

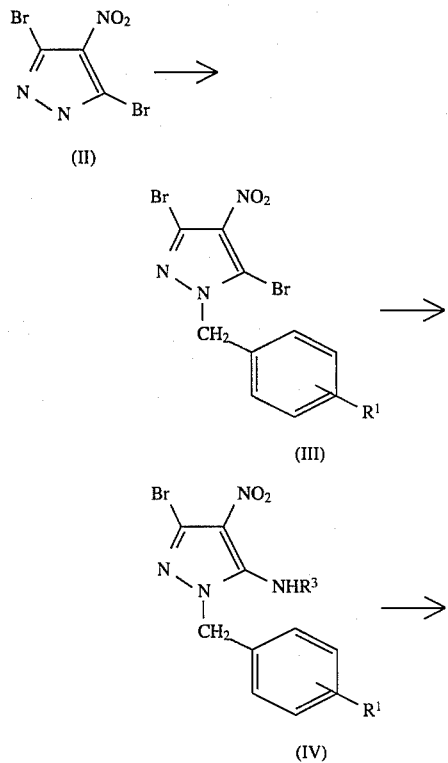

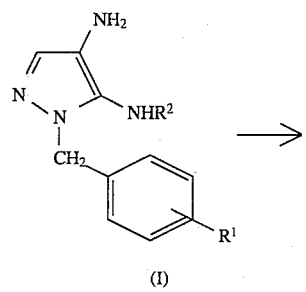

The 3,5-dibromo-4-nitropyrazole (II) used as starting material is described in the pertinent literature and can be produced as follows:

Nitration of pyrazole with a mixture of sulfuric acid and nitric acid produces 4-nitropyrazole in a yield of 80 percent (R. Hüttel, et al., *Chem. Ber.* 88, p. 1577 (1955)). N-nitropyrazole is obtained in yields of 84 to 93 percent under milder conditions during nitration (H. J. Klebe, et al., *Synthesis* 1973, p. 294) and can be rearranged to give 4-nitropyrazole by interaction with sulfuric acid (R. Hüttel, et al., *Chem. Ber.* 88, p. 1586 (1955)). Bromination of 4-nitropyrazole according to J. P. H. Juffermanns, et al., *J. Org. Chem.* 51, p. 4656 (1986) gives 3,5-dibromo-4-nitropyrazole (II).

In the process according to the invention, 3,5-dibromo-4-nitropyrazole can be converted to the new 1-benzyl-substituted pyrazoles of the general formula (III), where $R^1$ is a halogen, alkyl or alkoxy radical. These radicals can be introduced by various methods. For example, the compounds of general formula (III) can be obtained by converting compound (II) with sodium hydride in dimethylformamide by adding suitable benzyl halides. The particular advantage of this reaction step consists chiefly in the production of isomer-pure N-benzylsubstituted pyrazoles of the general formula (III).

By exchanging a bromine atom in compound (III), the pyrazole derivatives of the general formula (IV) are obtained, where $R^1$ represents a halogen, alkyl or alkoxy radical and $R^3$ represents a $C_1$–$C_4$-alkyl radical, a $C_2$–$C_4$-hydroxyalkyl or benzyl radical. The bromine atom is exchanged by interaction with an aqueous or alcoholic solution of the corresponding alkyl amine, hydroxyalkyl amine or benzyl amine. The bromine atom is exchanged exclusively in the 5-position in this reaction step so that only isomer-pure compounds result in this reaction step also.

The compounds of the general formula (IV) can be converted to different 4,5diaminopyrazoles of the general formula (I) by catalytic reduction. This reduction is normally carried out with hydrogen and common catalysts (e.g. palladium/activated carbon catalysts) and, if necessary, hydrogenation can be effected under pressure in an autoclave to increase the reaction rate. In this process, it is particularly surprising that the substituted benzyl radical of the compound of general formula (IV) is not removed by reduction. In contrast, 4,5-diaminopyrazoles carrying a hydrogen atom in the 1-position were obtained after reduction in all cases in comparison tests with compounds of formula (IV) in which $R^1$ represents hydrogen.

With respect to compounds of general formula (IV), where $R^3$ represents a benzyl radical or a tertiary butyl radical, 4,5-diaminopyrazole derivatives carrying, as before, a substituted benzyl radical in the 1-position are obtained after removal of these radicals by reduction.

In principle, corresponding compounds of formula (IV) could also be obtained when the bromine atom in the 5-position is exchanged for an amino group in producing the compounds of general formula (III). However, this reaction was not observed under the usual reaction conditions; even at increased pressure the introduction of an amino group in preparative yields was not successful.

The salts of the compounds of formula (I) can be obtained by conversion with organic or inorganic acids or bases.

The developers of formula (I) are used in the hair dye composition either as free bases or in the form of their physiologically tolerated salts with inorganic or organic acids, e.g. hydrochloric acid, sulfuric acid, phosphoric acid, acetic acid, propionic acid, lactic acid or citric acid. The compounds of formula (I) are favorably soluble in water and have, in addition, an excellent shelf stability, particularly as a component of the hair dye composition herein described.

The hair dye composition, according to the invention, containing 4,5-diaminopyrazole derivatives as developers produces in hair coloring with excellent color fastness, particularly with respect to light fastness, washing fastness and rubbing fastness.

With respect to dyeing characteristics, the hair dye composition according to the invention offers possibilities reaching far beyond the replacement of commonly used 4-aminophenols. Brilliant red shades with extraordinary depth of color can be produced, which is not possible with the current dye components. But apart from its use for fashion shades, natural color shades can also be produced by using the composition in combination with suitable coupling components without requiring an additional developing component of the p-phenylenediamine type.

The very good dyeing properties of the hair dye composition according to the present application are also evident in that this composition enables graying hair having previous chemical damage to be dyed easily and with good covering power.

Further, the subject matter of the present patent application concerns new 4,5-diaminopyrazole derivatives of the general formula (I), in particular 4,5-diamino-1-(4'-methoxybenzyl)pyrazole, 4,5-diamino-1-(3'-methoxybenzyl)pyrazole, 4,5-diamino-1-(4'-methylbenzyl)pyrazole, 4,5-diamino-1-(4'-chlorobenzyl)pyrazole, 4-amino-1-(4'-methoxybenzyl)-5-methylaminopyrazole and 4-amino-5-(2'-hydroxyethyl)amino- 1-(4'-methoxybenzyl)pyrazole.

The following examples explain the subject matter of the invention in more detail without the invention being limited to these examples.

PRODUCTION EXAMPLES

Example 1

Synthesis of 1-benzyl-3,5-dibromo-4-nitropyrazoles of general formula (III)

General directions 19.0 g (70 mmoles) of 3,5-dibromo-4-nitropyrazole in 90 ml absolute dimethylformamide (DMF) are added dropwise to 1.75 g (70 mmoles) of sodium hydride (96% in 150 ml absolute DMF) over a period of 1 hour. An increased temperature in the reaction solution and substantial gas generation are observed. As soon as the gas generation has subsided, a clear orange solution is present. 70.0 mmoles of benzyl halide in 30 ml DMF are added by drops and heating is carried out at 80° C. for 3 hours. The solvent is then vacuum-distilled and the residue is recrystallized from methylene chloride.

I. 3,5-dibromo-1-(4'-methoxybenzene)-4-nitropyrazole Benzyl halide: 4-methoxybenzyl chloride According to the general directions, 21.7 g (79 percent of theory) of 3,5-dibromo- 1-(4'-methoxybenzyl)-4-nitropyrazole are obtained with a melting point of 115° to 118°C.

$^1$H-NMR (60 MHz, DMSO-$d_6$):$\delta$=3.78 (s; 3H; OCH$_3$); 5.30 (s; 2H;—CH$_2$—) and 7.07 ppm (m; 4H; Ph-H)

MS (70 eV): m/e=393 (M$^+$).

II. 3,5-dibromo-1-(3'-methoxybenzyl)-4-nitropyrazole Benzyl halide: 3-methoxybenzyl chloride According to the general directions, 26 g (96 percent of theory) of 3,5-dibromo-1-(3'-methoxybenzyl)-4-nitropyrazole are obtained with a melting point of 130° C.

$^1$H-NMR (MHz), DMSO-$d_6$:$\delta$=3.74 (s; 3H; OCH$_3$); 5.48 (s; 2H;—CH$_2$—), 6.76–6.93 (m; 3H; 3H; Ph-H) and 7.30 ppm (dd; J-8 Hz; 1H; Ph-5H)

MS (70 eV): m/e=393 (M$^+$).

III. 3,5-dibromo-1-(4'-methylbenzyl)-4-nitropyrazole Benzyl halide: 4-methylbenzyl chloride According to the general directions, 18 g (68 percent of theory) of 3,5-dibromo-1-(4'-methylbenzyl)-4-nitropyrazole are obtained with a melting point of 108° C.

$^1$H-NMR (300 MHz, DMSO-$d_6$):$\delta$=2.28 (s; 3H;—CH$_3$); 5.45 (s; 2H;—CH$_2$—) and 7.18 ppm (m; 4H; Ph-H)

MS (70 eV): m/e=375 (M$^+$).

IV. 3,5-dibromo-1-(4'-chlorobenzyl)-4-nitropyrazole Benzyl halide: 4-chlorobenzyl chloride According to the general directions, 25 g (91 percent of theory) of 3,5-dibromo-1-(4'-chlorobenzyl)-4-nitropyrazole are obtained with a melting point of 109° C.

$^1$H-NMR (300 MHz, DMSO-$d_6$):$\delta$=5.51 (s; 2H;—CH$_2$); 7.28 (d; J=8.4 Hz; 2H; Ph-3H and Ph-5H) and 7.75 ppm (d; J=8.4 Hz; 2H; Ph-2H and Ph-6H)

MS (70 eV): m/e=395 (M$^+$).

Example 2

Synthesis of 5-alkylamino-1-benzyl-3-bromo-4-nitropyrazoles of general formula (IV)

I. Production of 3-bromo-1-(4'-methoxybenzyl)-5-methylamino-4-nitropyrazole 3.93 g (10.0 mmoles) of 3,5-dibromo-1-(4'-methoxybenzyl)-4-nitropyrazole are mixed with 100 ml of a 40-percent aqueous methylamine solution (1.28 moles) while stirring. The color of the reaction solution changes to yellow. The reaction mixture is stirred overnight at 60 degrees Celsius. The yellow-orange solution from which a yellow substance is already crystallized extracted three times with 200 ml acetic acid in each instance, dried over calcium chloride and the oily residue is filtered over silica gel with methylene chloride.

Yield: 2.54 g (75 percent of theory) of 3-bromo-1-(4'-methoxybenzyl)-5-methylamino-4-nitropyrazole in the form of yellow crystals with a melting point of 144 to 147 degrees Celsius.

$^1$H-NMR (60 MHz, DMSO-$d_6$):$\delta$=7.67 (q; 1H; J=6 Hz; —NH; exchangeable with D$_2$O), 7.00 (m; 4H; Ph-H), 5.33 (s; 2H;—CH$_2$PH-OCH$_3$) 3.72 (s; 3H;—OCH$_3$) and 3.05 ppm (d; 3H; J=6 Hz;—CH$_3$) MS (70 eV): m/e=342 (M$^+$).

II. Synthesis of 3-bromo-5-(2'-hydroxethylamino)-1-(4'-methoxybenzyl)-4-nitropyrazole 4.00 g (10.0 mmoles) of 3,5-dibromo-1-(4'-methoxybenzyl)-4-nitropyrazole are mixed in 30 ml ethanol with 0.61 g (10.0 mmoles) of ethanolamine and stirred overnight at 70 degrees Celsius. A thin-layer chromatograph shows that a conversion of approximately 50 % was effected. Another 0.60 g (10.0 mmoles) of ethanolamine are added and the mixture is stirred for 2 hours at 70 degrees Celsius. An individual reaction product is found in the thin-layer chromatograph (solvent: methylene chloride) in addition to a little educt. The reaction mixture is poured on water and a yellow substance is crystallized and collected by suction filtration.

Yield: 3.39 g (91 percent of theory) of 3-bromo-5-(2-hydroxyethylamino)-1-(4-methoxybenzyl)-4-nitropyrazole with a melting point of 112 degrees Celsius.

$^1$H-NMR (60 MHz, DMSO-d$_6$):δ=7.50 (s;wide; 1H; —NH; exchangable with D$_2$O), 7.05 (m; 4H; Ph-H), 5.34 (s; 2H; CH$_2$—PH—OCH$_3$), 5.00 (s; 3H; wide; 1H;—OH; exchangeable with D$_2$O), 3.75 (s; 3H; —OCH$_3$) and 3.45 ppm (m; 4H;—CH$_2$—CH$_2$—)

MS (70 eV): m/e=372 (M$^+$)

III. Synthesis of 3-bromo-5-tert-butylamino-1-(4'-methoxybenzyl)-4'-nitropyrazole 0.50 g (1.28 mmoles) of 3,5-dibromo-1-(4'-methoxybenzyl)-4-nitropyrazole are heated in a solution of 10 g of tert-butylamine in 40 ml ethanol for 20 hours under reflux. After cooling, the reaction mixture is poured in 100 ml water and extracted three times with 50 ml acetic acid in each instance. After drying over magnesium sulfate, the mixture is rotated and the residue is filtered by adsorption on silica gel with dichloromethane.

Yield: 490 mg (99 percent of theory) of 3-bromo-5-tert-butylamino-1-(4'-methoxybenzyl)-4-nitropyrazole as pale yellow crystals with a melting point of 72 degrees Celsius.

$^1$H-NMR (60 MHz, DMSO-d$_6$):δ=7.00 ppm (m; 4H; Ph-H), 5.32 (s; 1H; N—H; exchangeable with D$_2$O), 5.22 (s; 2H; 1N—CH$_2$—), 3.70 (s; 3H; OCH$_3$), and 1.18 ppm (s; 9H;—C(CH$_3$)$_3$)

MS (70 eV): m/e=394 (M$^+$)

IV. Synthesis of 5-benzylamino-3-bromo-1-(4'-methoxybenzyl)-4-nitropyrazole 4.00 g (10.0 mmoles) of 3,5-dibromo-1-(4'-methoxybenzyl)-4-nitropyrazole are mixed in 30 ml ethanol with 11.0 g (100 mmoles) of benzylamine. This is heated at boiling temperature for 3.5 hours. The reaction mixture is poured on 100 ml water and extracted two times with 100 ml acetic acid in ethyl ester each instance. After drying with magnesium sulfate, the oily residue is filtered by adsorption on silica gel with a mixture of hexane and chloroform (1:2).

Yield: 4.13 g (99 percent of theory) of 5-benzylamino-3-bromo-1-(4'-methoxybenzyl)-4-nitropyrazole with a melting point of 125 to 127 degrees Celsius (hexane/chloroform 1:2).

$^1$H-NMR (60 MHz, DMSO-d$_6$):δ=7.93 (t; 1H; J=6 Hz; —NH; exchanges with D$_2$O), 7.40–6.80 (m; 9H; Ph-H), 5.15 (s; 2H; CH$_3$O-Ph-CH$_2$), 4.58 (d; 2H; J=6 Hz; —NH—CH$_2$—; s after exchange with D$_2$O), and 3.73 ppm (s; 3 Hz; —OCH$_3$)

MS (70 eV): m/e=418 (M$^+$)

V. Synthesis of 5-benzylamino-3-bromo-1-(4'-methylbenzyl)-4-nitropyrazole 15 g (40 mmoles) of 3,5-dibromo-1-(4'-methylbenzyl)-4-nitropyrazole are mixed in 120 ml ethanol with 15 ml benzylamine. After heating for 1 hour, it is poured on ice, suctioned and recrystallized from ethanol.

Yield: 10.0 g (62 percent of theory) of 5-benzylamino-3-bromo-1-(4'-methylbenzyl)-4-nitropyrazole with a melting point of 108 degrees Celsius.

$^1$H-NMR (300 MHz,DMSO-d$_6$):δ=2.29 (s; 3H;—CH$_3$ ); 4.54 (d; J=6.4 Hz; 2H; NH—CH$_2$—; s after exchange with D$_2$O); 5.51 (s; 2H; 1-CH$_2$); 7.15–7.35 (m; 9H; Ph-H) and 8.00 ppm (t; J=6.4 Hz; 1H; NH; exchanges with D$_2$O)

MS (70 eV): m/e=400 (M$^+$)

VI. Synthesis of 5-benzylamino-3-bromo-1-(4'-chlorobenzyl)-4-nitropyrazole 9.88 g (25 mmoles) of 3,5-dibromo-1-(4'-chlorobenzyl)-4-nitropyrazole are heated for 1 hour in 50 ml ethanol with 15 ml benzylamine. The mixture is poured on ice, collected by suction and recrystallized from ethanol.

Yield: 8 g (76 percent of theory) of 5-benzylamino-3-bromo-1-(4'-chlorobenzyl)-4nitropyrazole with a melting point of 139 to 141 degrees Celsius.

$^1$H-NMR (300 MHz, DMSO-d$_6$):δ=4.54 (d; J=5.4 Hz; 2H; 2H; NH—CH$_2$—; s after exchange with D$_2$O); 5.23 (s; 2H; 1—CH$_2$—); 7.10–7.38 (m; 9H; Ph-H) and 8.00 (t; 1H; —NH; exchanges with D$_2$O)

MS (70 eV): m/e=421 (M$^+$)

VII. Synthesis of 5-benzylamino-3-bromo-1-(3'methoxybenzyl)-4-nitropyrazole 7.8 g (20 mmoles) of 3,5-dibromo-1-(3'-methoxybenzyl)-4-nitropyrazole are heated for 1 hour in 15 ml benzylamine at 80 degrees Celsius. The mixture is poured on ice, collected by suction and recrystallized from ethanol.

Yield: 5.8 g (70 percent of theory) of 5-benzylamino-3-bromo-1-(3'-methoxybenzyl)-4nitropyrazole with a melting point of 98 degrees Celsius.

$^1$H-NMR (300 MHz, DMSO-$_6$):δ=4.54 (d; J=6.0 Hz; 2H; NH—CH$_2$—; s after exchange with D$_2$O); 5.19 (s; 2H; 1-CH$_2$—); 6.00–7.33 (m; 9H; Ph-H) and 8.02 (t; J=6.0 Hz; 1H, NH; exchanges with D$_2$O)

MS (70 eV): m/e=417 (M$^+$)

Example 3

Synthesis of 1-benzyl-4,5-diaminopyrazoles of general formula (I)

Hydrogenation of 5-alkylamino-1-benzyl-3-bromo-4-nitropyrazoles of general formula (IV).

General directions A:

1-Alkyl-5-aminoalkyl-3-bromo-4-nitropyrazole is mixed with 130 ml ethanol and 2 spatula tips of palladium/activated carbon catalyst (10 %) and transferred to an autoclave (250 ml) and stirred at 50 bar hydrogen atmosphere at room temperature (20 to 30 degrees Celsius) for the indicated period. At the conclusion of the reaction, the reaction mixture is transferred to a glass flask via a glass filter pump and is immediately filtered over glass frit. The filtrate is mixed with an equimolar amount of concentrated sulfuric acid (97%).

I. Synthesis of 4-amino-1-(4'-methoxybenzyl)-5-methylaminopyrazole 1.04 g (3.00 mmoles) of 3-bromo-1-(4'-methoxybenzyl)-5-methylamino-4-nitropyrazole are hydrogenated for 2 hours according to General Directions A. 0.30 g (2.80 mmoles) of concentrated sulfuric acid (97%) are added. After reduction, 0.86 g (87 percent of theory) of 4-amino-1-(4'-methoxybenzyl)-5-methylaminopyrazole hydrosulfate are obtained in the form of an oil.

$^1$H-NMR (60 MHz, DMSO-d$_6$);δ=9.60–7.73 (s; wide; 7H; —NH; —NH$_2$; H$_2$SO$_4$; exchangeable with D$_2$O); 7.51 (s; 1H; 3-H), 7.02 (m; 4H; Ph-H), 5.13 (s; 2H; —CH$_2$-Ph-OCH$_3$), 3.70 (s; 3H; —OCH$_3$), and 2.80 ppm (s; 3H; CH$_3$NH—)

MS (70 eV): m/e=232 (M$^+$)

II. Synthesis of 4-amino-5-(2'-hydroxyethylamino)-1-(4'-methoxybenzyl)pyrazole 1.04 g (2.80 mmoles) of 3-bromo-5-(2'-hydroxyethylamino)-1-(4'-methoxybenzyl)-4-nitropyrazole are hydrogenated for 3 hours according to General Directions A. 0.81 g (80 percent of theory) of 4-amino-5-(2'-hydroxyethylamino)-1-(4'-methoxybenzyl)pyrazole hydrosulfate are obtained in the form of an oil.

$^1$H-NMR (60 MHz, DMSO-$d_6$):δ=8.66–3.83 (s; wide; 9H; —NH; —NH$_2$—OH, H$_2$SO$_4$ exchangeable with D$_2$O); 7.37 (s; 1H; 3-H), 7.00 (m; 4H; Ph-H), 5.13 (s; 2H; —CH$_3$O-Ph-CH2—), 3.73 (s; 3H; —OCH$_3$), and 3.67–3.32 ppm (m; 4H; —CH$_2$-CH$_2$—)

MS (79 eV): m/e=262 (M$^+$)

III. Synthesis of 4,5-diamino:-1-(4'-methoxybenzyl)pyrazole a) 1.00 g (2.40 mmoles) of 5-benzylamino-3-bromo-1-(4'-methoxybenzyl)-4-nitropyrazole are hydrogenated for 3 hours according to directions A.

Yield: 590 mg (78 percent of theory) of 4,5-diamino-1-(4'-methoxybenzyl)pyrazole hydrosulfate with a melting point of 186 to 187 degrees Celsius.

$^1$H-NMR (60 MHz, DMSO-$d_6$):δ=9.10–5.51 (s; wide; 7H; 2 —NH$_2$; H$_2$SO$_4$; exchangeable with D$_2$O); 7.30 (s; 1H; 3-H), 7.05 (m; 4H; Ph-H), 5.12 (s; 2H; CH$_3$O-Ph-CH$_2$—) and 3.73 ppm (s; 3H; —OCH3)

MS (70 eV) :m/e=218 (M$^+$)

b) 260 mg (0.68 mmoles) of 3-bromo-5-tert-butylamino-1-(4'-methoxybenzyl)-4-nitropyrazole are mixed in 100 ml absolute ethanol with 2 spatula tips of palladium-activated carbon catalyst and hydrogenated for 2 hours at 50 bar at room temperature.

Yield: 170 mg (79 percent of theory) of 4,5-diamino-1-(4'-methoxybenzyl)pyrazole hydrosulfate with a melting point of 186 to 187 degrees Celsius.

IV. Synthesis of 4,5-diamino-1-(3'-methoxybenzyl)pyrazole 1.64 g (4 mmoles) of 5-benzylamino-3-bromo-1-(3'-methoxybenzyl)-4-nitropyrazole are hydrogenated for 4 hours according to directions A. 1.0 g (82 percent of theory) of 4,5-diamino-1-(3'-methoxybenzyl)pyrazole hydrosulfate are obtained with a melting point of 185 degrees Celsius (with decomposition).

$^1$H-NMR (300 MHz, DMSO-$d_6$):δ=7.43 (s; 1H; 3-H), 7.23 (dd; J=7.2 Hz and 8.1 Hz; 1H; Ph-3H); 6.84 (d; J=8.3 Hz; 1H; Ph-4H); 6.73 (s; 1H; Ph-1H); 6.71 (d; J=7Hz; 1H; Ph-2H); 6.5–5.5 (s; wide; 6H; NH$_2$; H$_2$SO$_4$; exchanges with D$_2$O); 5.18 (s; 2H; —CH$_2$—) and 3.70 ppm (s; 3H; —OCH3)

MS (70 eV) :m/e=218 (M$^+$)

V. Synthesis of 4.5-diamino-1-(4'methylbenzyl)pyrazole 3.0 g (7.5 mmoles)of 5-benzylamino-3-bromo-1-(4'-methylbenzyl)-4-nitropyrazole are hydrogenated for 4 hours according to directions A. 1.90 g (84 percent of theory) of 4,5-diamino-1-(4'-methylbenzyl)pyrazole hydrosulfate are obtained with a melting point of 163 to 167 degrees Celsius (with decomposition).

$^1$H-NMR (300 MHz, DMSO-$d_6$):δ=7.31 (s; 1H; 3-H), 7.2–7.05 (m;4H; Ph-H); 5.8–6.7 (s; 6H; NH$_2$; H$_2$SO$_4$; exchanges with D$_2$O); 5.12 (s; 2H; —CH$_2$—) and 2.26 ppm (s; 3H; —CH$_3$)

MS (70 eV): m/e=202 (M$^+$)

VI. Synthesis of 4,5-diamino-1-(4'-chlorobenzyl)pyrazole 3.15 g (7.5 mmoles) of 5-benzylamino-3-bromo-1-(4'-chlorobenzyl)-4-nitropyrazole are hydrogenated for 3 hours according to directions A. 2 g (82 percent of theory) of 4,5-diamino-1-(4'-chlorobenzyl)pyrazole hydrosulfate are obtained with a melting point of 188 degrees Celsius (with decomposition).

$^1$H-NMR (300 MHz, DMSO-$d_6$):δ=7.13–7.39 (m; 5H; 3-H and Ph-H), 6.0–6.8 (s; wide; 6H; NH$_2$; H$_2$SO$_4$; exchanges with D$_2$O) and 5.12 ppm (s; 2H; —CH$_2$—)

MS (70 eV): m/e=222 (M$^+$)

For all NMR spectra:
s=singlet, d=doublet, t=triplet, q=quartet, m=multiplet

HAIR DYE EXAMPLES

Example 4

Hair dye composition in gel form

| | |
|---|---|
| 1.51g | 4,5-diamino-1-(4'-methoxybenzyl)pyrazole hydrosulfate |
| 0.65g | 5-amino-2-methylphenol |
| 0.15g | sodium sulfite |
| 5.00g | lauryl alcohol diglycol ether sulfate sodium salt (28-percent aqueous solution) |
| 1.00g | hydroxyethylcellulose, highly viscous |
| 10.00g | ammonia (22-percent aqueous solution) |
| 81.69g | water |
| 100.00g | |

50 g of the hair dye composition indicated above are mixed with 50 g hydrogen peroxide solution (6-percent) shortly before use and the mixture is then applied to blond natural hair and allowed to act at 40 degrees Celsius for 30 minutes. The hair is then rinsed with water and dried. The hair is dyed an intensive brilliant red-orange color.

Example 5

Hair dye solution

| | |
|---|---|
| 1.60g | 4,5-diamino-1-(3'-methoxybenzyl)pyrazole hydrosulfate |
| 0.45g | 3-aminophenol |
| 0.30g | 2-amino-4-(2'-hydroxyethyl)aminoanisole sulfate |
| 10.00g | lauryl alcohol diglycol ether sulfate sodium salt (28-percent aqueous solution) |
| 10.00g | ammonia (22-percent aqueous solution) |
| 77.65g | water |
| 100.00g | |

50 g of the hair dye composition indicated above are mixed with 50 g hydrogen peroxide solution (6-percent) shortly before use and the mixture is then applied to blond natural hair and allowed to act at 40 degrees Celsius for 30 minutes. The hair is then rinsed with water and dried. The hair is dyed a fashionable bordeaux shade.

Examples 6 to 23

Hair dye solutions

Hair dye solutions with the following composition are produced:

| | |
|---|---|
| 0.025 mole | developer according to TABLE 1 |
| 0.025 mole | coupler according to TABLE 1 |
| 10.00 g | lauryl alcohol diglycol ether sulfate sodium salt (28-percent aqueous solution) |
| 10.00 g | ammonia (22-percent aqueous solution) |
| to 100.00 g | water |
| 100.00 g | |

The hair dye solutions are prepared according to Example 5 and applied to 90-percent gray human hair. The resulting colorings are shown in Table 1.

TABLE 1

| Example | developer of formula (I) from production example | coupler | color |
|---|---|---|---|
| 6 | 3/I | 5-amino-2-methylphenol | bright red |
| 7 | 3/II | 5-amino-2-methylphenol | red |
| 8 | 3/III | 5-amino-2-methylphenol | bright orange |
| 9 | 3/IV | 5-amino-2-methylphenol | bright orange |
| 10 | 3/V | 3-aminophenol | red |
| 11 | 3/VI | 3-aminophenol | bright red |
| 12 | 3/I | 2-amino-4-(2'-hydroxyethyl)-aminoanisole sulfate | blue-violet |
| 13 | 3/II | 2-amino-4-(2'-hydroxyethyl)-aminoanisole sulfate | violet |
| 14 | 3/III | 2-amino-4-(2'-hydroxyethyl)-aminoanisole sulfate | dark violet |
| 15 | 3/IV | 2-amino-4-(2'-hydroxyethyl)-aminoanisole sulfate | dark violet |
| 16 | 3/V | 4-(2'-hydroxyethyl)amino-1,2-methylenedioxybenzene | dark red |
| 17 | 3/VI | 4-(2'-hydroxyethyl)amino-1,2-methylenedioxybenzene | dark red |
| 18 | 3/I | α-naphthol | brownish red |
| 19 | 3/II | α-naphthol | violet |
| 20 | 3/III | α-naphthol | bright violet |
| 21 | 3/IV | α-naphthol | bright violet |
| 22 | 3/V | α-naphthol | bright violet |
| 23 | 3/VI | α-naphthol | light violet |

We claim:

1. Composition for oxidative dyeing of hair based on a combination of developer substances and coupler substances, containing as a developer substance a 4,5-diaminopyrazole selected from the group consisting of 4,5-diamino-1-(4'-methoxybenzyl)pyrazole, 4,5-diamino-1-(4'-methylbenzyl)pyrazole, 4,5-diamino-1-(4'-chlorobenzyl)pyrazole, 4,5-diamino-1-(3'-methoxybenzyl)pyrazole, 4-amino-1-(4'-methoxybenzyl)-5-methylaminopyrazole and 4-amino-5-(2'-hydroxyethyl)amino-1-(4'-methoxybenzyl)pyrazole.

2. Composition according to claim 1, wherein the developer substance is contained in a quantity of 0.01 to 3.0 percent by weight.

3. Composition according to claim 1 wherein said coupler substance is selected from the group consisting of α-naphtol, resorcinol, 4-chlororesorcinol, 4,6-dichlororesorcinol, 2-methylresorcinol, 2-amino-4-(2'-hydroxyethyl)aminoanisole, 5-amino-2-methylphenol, 3-amino-2-methylphenol, 4-hydroxy-1,2-methylenedioxybenzene, 4-amino-1,2-methylenedioxybenzene, 4-(2'-hydroxyethyl)amino-1, 2-methylenedioxybenzene, 2,4-diaminophenetole, 2,4-diamino-5-methylphenetole, 2,4-diaminobenzyl alcohol, m-phenylenediamine, 2,4-diaminophenoxyethanol, 4-hydroxyindole, 3-amino-5-hydroxy-2,6-dimethoxypyridine and 3,5-diamino-2,6-dimethoxypyridine.

4. Composition according to claim 1, wherein the total quantity of the combination of developer substances and coupler substances is from 0.1 to 5.0 percent by weight.

5. Composition according to claim 1, further comprising a member selected from the group consisting of 6-amino-2-methylphenol, 2-amino-5-methylphenol, 4-[(4'-aminophenyl)-(4"-imino-2", 5"cyclohexadiene -1-ylidene)methyl]-2-methylaminobenzene monohydrochloride, 4-[(4'-amino-3'-methylphenyl) -(4"-imino-3"-methyl-2",5"-cyclohexadiene-1"-ylidene)methyl]-2-methylaminobenzene monohydrochloride, 2-nitro-1,4-diaminobenzene, 2-amino-4-nitrophenol, 2-amino-5-nitrophenol, 2-amino-4,6-dinitrophenol, 2-amino-5-(2'-hydroxyethyl)aminonitrobenzene, 2-methylamino-5-bis-(2'-hydroxyethyl)aminonitrobenzene, 6-[(4'-aminophenyl)azo]-5-hydroxynaphthalene-1-sulfonic acid sodium salt, 1,4-diaminoanthraquinone and 1,4,5,8-tetraaminoanthraquinone.

6. 4,5-Diamino-1-(4'-methoxybenzyl)pyrazole.

7. 4,5-Diamino-1-(4'-methylbenzyl)pyrazole.

8. 4,5-Diamino- 1 -(4'-methoxybenzyl)pyrazole.

9. 4,5-Diamino- 1-(3'-methylbenzyl)pyrazole.

10. 4-Amino-1-(4'-methyoxybenzyl)-5-methylaminopyrazole.

11. 4-Amino-5-(2'-hydroxyethyl)amino- 1-(4'-methoxybenzyl)pyrazole.

* * * * *